(12) United States Patent
Dannaher et al.

(10) Patent No.: US 10,459,740 B2
(45) Date of Patent: Oct. 29, 2019

(54) SYSTEM AND METHOD TO ESTABLISH CURRENT SETPOINT FOR ULTRASONIC TRANSDUCER

(71) Applicant: Ethicon Endo-Surgery, LLC, Guaynabo, PR (US)

(72) Inventors: William D. Dannaher, Cincinnati, OH (US); Patrick A. Weizman, Liberty Township, OH (US); Eitan T. Wiener, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 452 days.

(21) Appl. No.: 15/060,684

(22) Filed: Mar. 4, 2016

(65) Prior Publication Data

US 2017/0255479 A1    Sep. 7, 2017

(51) Int. Cl.
| | |
|---|---|
| *G06F 9/445* | (2018.01) |
| *A61B 34/00* | (2016.01) |
| *A61B 17/32* | (2006.01) |
| *A61B 17/00* | (2006.01) |

(52) U.S. Cl.
CPC .. *G06F 9/44505* (2013.01); *A61B 17/320068* (2013.01); *A61B 34/25* (2016.02); *A61B 2017/00039* (2013.01); *A61B 2017/00132* (2013.01); *A61B 2017/00477* (2013.01); *A61B 2017/320071* (2017.08)

(58) Field of Classification Search
CPC ............ A61B 34/25; A61B 17/320068; A61B 18/1206; A61B 2018/00636–00892; A61B 2018/00988
See application file for complete search history.

(56) References Cited

U.S. PATENT DOCUMENTS

| | | |
|---|---|---|
| 5,322,055 A | 6/1994 | Davison et al. |
| 5,873,873 A | 2/1999 | Smith et al. |
| 5,980,510 A | 11/1999 | Tsonton et al. |
| 6,325,811 B1 | 12/2001 | Messerly |
| 6,773,444 B2 | 8/2004 | Messerly |
| 6,783,524 B2 | 8/2004 | Anderson et al. |
| 8,095,327 B2 | 1/2012 | Tahara et al. |
| 8,461,744 B2 | 6/2013 | Wiener et al. |
| 8,591,536 B2 | 11/2013 | Robertson |
| 8,623,027 B2 | 1/2014 | Price et al. |
| 8,986,302 B2 | 3/2015 | Aldridge et al. |

(Continued)

FOREIGN PATENT DOCUMENTS

| | | |
|---|---|---|
| EP | 1 199 043 A2 | 4/2002 |
| EP | 1 199 044 A1 | 4/2002 |

OTHER PUBLICATIONS

International Search Report and Written Opinion dated Jun. 21, 2017 for Application No. PCT/US2017/020138, 11 pgs.

*Primary Examiner* — Daniel W Fowler
*Assistant Examiner* — Catherine Premraj
(74) *Attorney, Agent, or Firm* — Frost Brown Todd LLC

(57) ABSTRACT

Systems, devices and methods manage surgical instruments throughout their lifecycle by reprogramming a device to account for operational displacement of ultrasonic components based upon a diagnostic test. A diagnostic test tip is used with a surgical instrument to simulate device usage and capture capacitance and phase margin of the device. This information is used to calculate an optimal current to supply to the device during future procedures.

15 Claims, 7 Drawing Sheets

(56) References Cited

U.S. PATENT DOCUMENTS

| | | | |
|---|---|---|---|
| 9,023,071 B2 | 5/2015 | Miller et al. | |
| 9,095,367 B2 | 8/2015 | Olson et al. | |
| 2002/0062132 A1* | 5/2002 | Kramer | A61B 17/320068 606/169 |
| 2002/0161385 A1* | 10/2002 | Wiener | A61B 17/320068 606/169 |
| 2002/0165680 A1* | 11/2002 | Wiener | A61B 17/320068 702/75 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2014/0005701 A1 | 1/2014 | Olson et al. | |

* cited by examiner

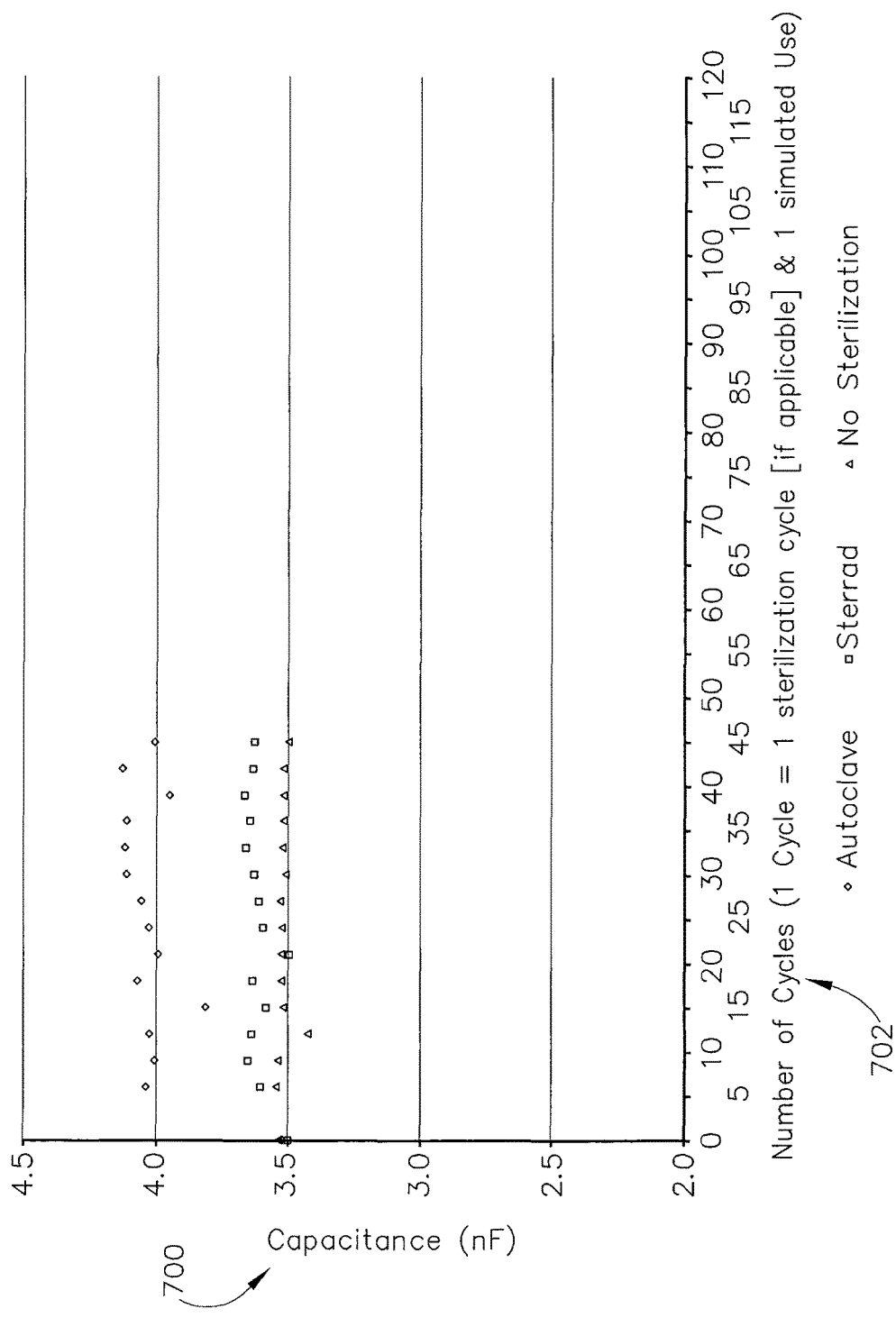

SYSTEM AND METHOD TO ESTABLISH CURRENT SETPOINT FOR ULTRASONIC TRANSDUCER

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 19, 2016, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

As a result of the critical nature of procedures performed with surgical instruments, extremely tight tolerances may be required both for newly manufactured instruments as well as for reusable instruments that have previously been put into service. While a particular surgical instrument may meet or exceed a specification at the time of manufacture, its performance may degrade after several uses due to normal wear and tear, or due to expansion of parts as a result of heat sterilization between uses. While manufacturers of such a product my provide guidelines for a number of uses before an instrument should be disposed, cost conscious end users may ignore such guidelines and create safety and usage issues for end users and patients.

While a variety of systems have been made and used for surgical device lifecycle management, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 7 depicts an exemplary graph plotting capacitance and number of cycles.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Overview of Exemplary Ultrasonic Surgical Instruments

Figure 1:
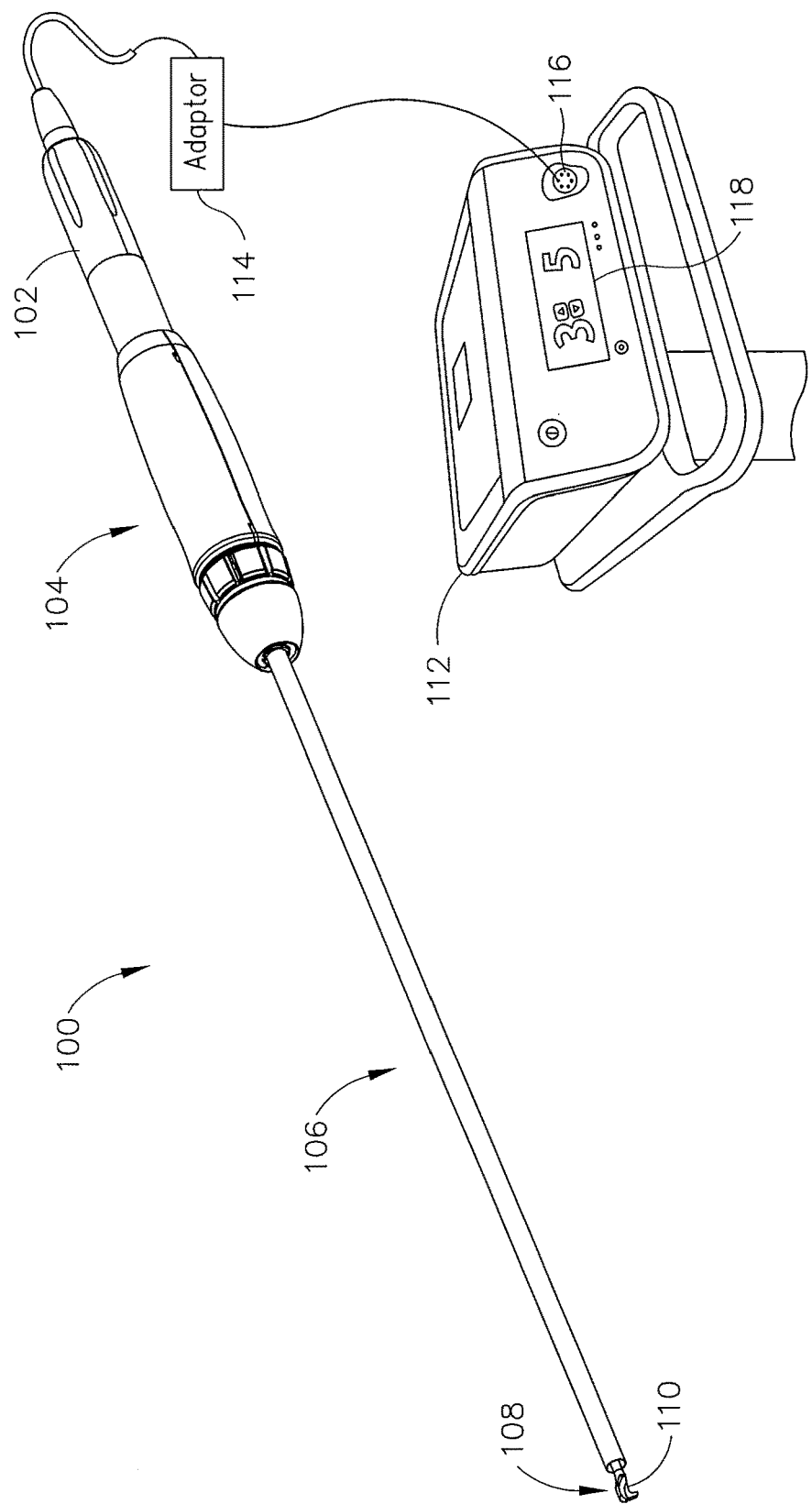
FIG. 1 depicts a perspective view of a first exemplary surgical instrument.

Turning now to the figures, FIG. 1 shows a perspective view of an exemplary surgical instrument (100). As described therein and as will be described in greater detail below, instrument (100) is operable to cut tissue and seal or weld tissue substantially simultaneously. It should also be understood that instrument (100) may have various structural and functional similarities with the HARMONIC SYNERGY® Ultrasonic Instrument. Furthermore, instrument (100) may have various structural and functional similarities with the devices taught in any of the other references that are cited and incorporated by reference herein.

Instrument (100) is configured to be used as a scalpel. As shown in FIG. 1, instrument (100) of this example comprises a handle assembly (104), a shaft assembly (106), and an end effector (108). The proximal end of instrument (100) receives and is fitted with an ultrasonic transducer assembly (102) by insertion of ultrasonic transducer assembly (102) into handle assembly (104). Handle assembly (104) is configured to receive ultrasonic transducer assembly (102) such that ultrasonic transducer assembly (102) may be coupled to an acoustic waveguide (not shown) in shaft assembly (106) by a threaded connection, though any other suitable type of coupling may be used. As shown in FIG. 1, instrument (100) may be coupled with ultrasonic transducer assembly (102) to form a single unit. Ultrasonic transducer assembly (102) includes a set of piezoelectric elements (not shown) that are located proximal to a horn (not shown) of the rigid acoustic waveguide. The piezoelectric discs are operable to convert electrical power into ultrasonic vibrations, which are then transmitted along acoustic waveguide, which extends through shaft assembly (106), to a blade (110) of end effector (108) in accordance with known configurations and techniques. By way of example only, this portion of the acoustic drivetrain may be configured in accordance with various teachings of various references that are cited herein.

Blade (110) may be integral with the acoustic waveguide (not shown) and formed as a single unit. In some versions, blade (110) may be connected to a waveguide by a threaded connection, a welded joint, and/or some other coupling feature(s). The distal end of blade (110) is disposed at or near a longitudinal position corresponding to an anti-node associated with ultrasonic vibrations communicated along a waveguide and blade (110) in order to tune the acoustic assembly to a preferred resonant frequency $f_o$ when the acoustic assembly is not loaded by tissue. When transducer assembly (102) is energized, the distal end of blade (110) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (110) may also vibrate in the y-axis at about 1 to about 10 percent of the motion in the x-axis. Of course, movement of blade (110) when transducer assembly (102) is energized may alternatively have any other suitable characteristics. When ultrasonic blade (110) is in an activated state (i.e., vibrating ultrasonically), ultrasonic blade (110) is operable to effectively cut through and seal tissue.

Transducer assembly (102) receives electrical power from a generator (112). In particular, transducer assembly (210) is coupled with generator (112) via an adaptor (114) and a cable (120) that is connected to a receptacle assembly (116) of generator (112). Receptacle assembly (116) provides a power and/or data input/output for connecting a surgical instrument (100) to the generator (112). Generator (112) of the present example further includes a display (118). Display (118) provides information on the generator (112) and any attached surgical instrument (100). In some versions, display (118) further provides controls or interfaces for allowing a user to change various settings of generator (112). Generator (112) further includes a power source and control module that is configured to provide a power profile to transducer assembly (102) that is particularly suited for the generation of ultrasonic vibrations through transducer assembly (102).

By way of example only, generator (112) may comprise a GEN 11 or GEN 300 sold by Ethicon Endo-Surgery, Inc. of Cincinnati, Ohio. In addition or in the alternative, generator (112) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. Still other suitable forms that generator (112) may take, as well as various features and operabilities that generator (112) may provide, will be apparent to those of ordinary skill in the art in view of the teachings herein. Adaptor (114) may also provide wider compatibility between a specific surgical instrument (100) and a specific receptacle (116) of generator (112); and may also enable additional functionality as described in further detail below.

Figure 2:
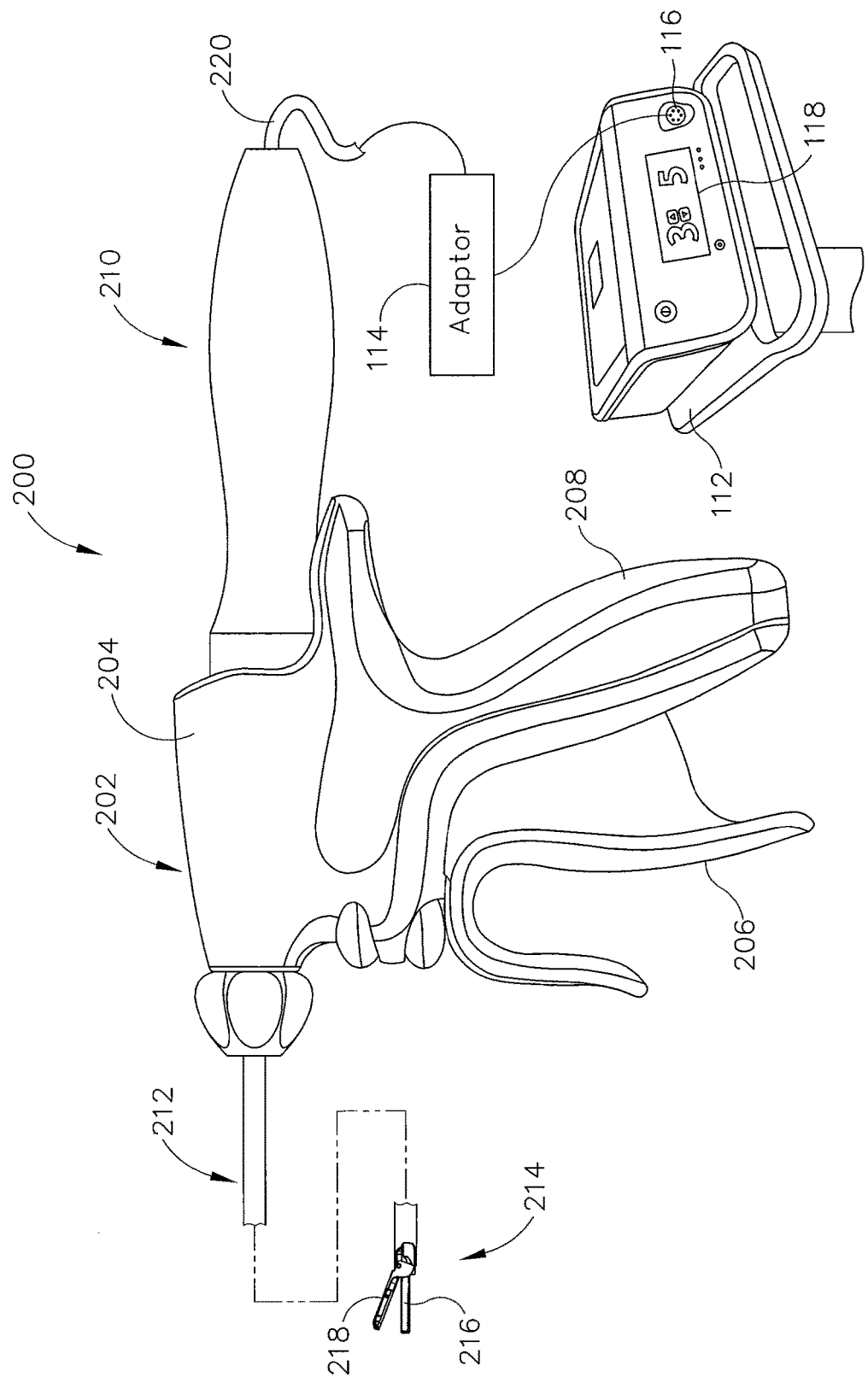
FIG. 2 depicts a side elevation view of a second exemplary surgical instrument.

FIG. 2 shows a side elevation view of another exemplary surgical instrument (200). Instrument (200) is operable to cut tissue and seal or weld tissue substantially simultaneously. It should also be understood that instrument (200) may have various structural and functional similarities with the HARMONIC ACE® Ultrasonic Shears. Furthermore, instrument (100) may have various structural and functional similarities with the devices taught in any of the other references that are cited and incorporated by reference herein.

Instrument (200) is configured to be used as a shears. Instrument (200) of this example comprises a handle assembly (202), a shaft assembly (212), and an end effector (214). Handle assembly (202) comprises a body (204) including a pistol grip (208) and a pair of buttons (126). Handle assembly (202) also includes a trigger (206) that is pivotable toward and away from pistol grip (208). It should be understood, however, that various other suitable configurations may be used, including but not limited to a pencil-grip configuration or a scissor-grip configuration. An ultrasonic transducer assembly (210) extends proximally from body (204) of handle assembly (202). Transducer assembly (210) is coupled with generator (112) via an adaptor (114) and a cable (220) connected to receptacle assembly (116). Transducer assembly (210) receives electrical power from generator (112) and converts that power into ultrasonic vibrations through piezoelectric elements. Generator (112) of the example shown in FIG. 2 is the same as the generator (112) of the example shown in FIG. 1. Other suitable forms that generator (112) may take will be apparent to those of ordinary skill in the art in view of the teachings herein.

End effector (214) includes an ultrasonic blade (216) and a pivoting clamp arm (218). Clamp arm (218) is coupled with trigger (206) such that clamp arm (218) is pivotable toward ultrasonic blade (216) in response to pivoting of trigger (206) toward pistol grip (208); and such that clamp arm (218) is pivotable away from ultrasonic blade (216) in response to pivoting of trigger (206) away from pistol grip (208). Various suitable ways in which clamp arm (218) may be coupled with trigger (206) will be apparent to those of ordinary skill in the art in view of the teachings herein.

Blade (216) of the present example is operable to vibrate at ultrasonic frequencies in order to effectively cut through and seal tissue, particularly when the tissue is being compressed between clamp arm (218) and blade (216). Blade (216) is positioned at the distal end of an acoustic drivetrain. This acoustic drivetrain includes transducer assembly (210) and an acoustic waveguide (not shown). Transducer assembly (210) includes a set of piezoelectric elements (not shown) that are located proximal to a horn (not shown) of the rigid acoustic waveguide. The piezoelectric discs are operable to convert electrical power into ultrasonic vibrations, which are then transmitted along acoustic waveguide, which extends through shaft assembly (212), to blade (216) in accordance with known configurations and techniques. By way of example only, this portion of the acoustic drivetrain may be configured in accordance with the teachings above and/or various teachings of various references that are cited herein. When ultrasonic blade (216) is in an activated state (i.e., vibrating ultrasonically), ultrasonic blade (216) is operable to effectively cut through and seal tissue, particularly when the tissue is being clamped between clamp arm (218) and ultrasonic blade (216).

Instruments (100, 200) shown in FIGS. 1-2 are merely illustrative examples of instruments that may be used with a generator (112) and an adaptor (114). By way of example only, either instrument (100, 200) may be modified and operable in accordance with the teachings of any of the various references that are cited herein. Other examples of suitable instruments will be apparent to those of ordinary skill in the art in view of the teachings herein.

II. Methods for Reprogramming an Ultrasonic Transducer

Figure 3:
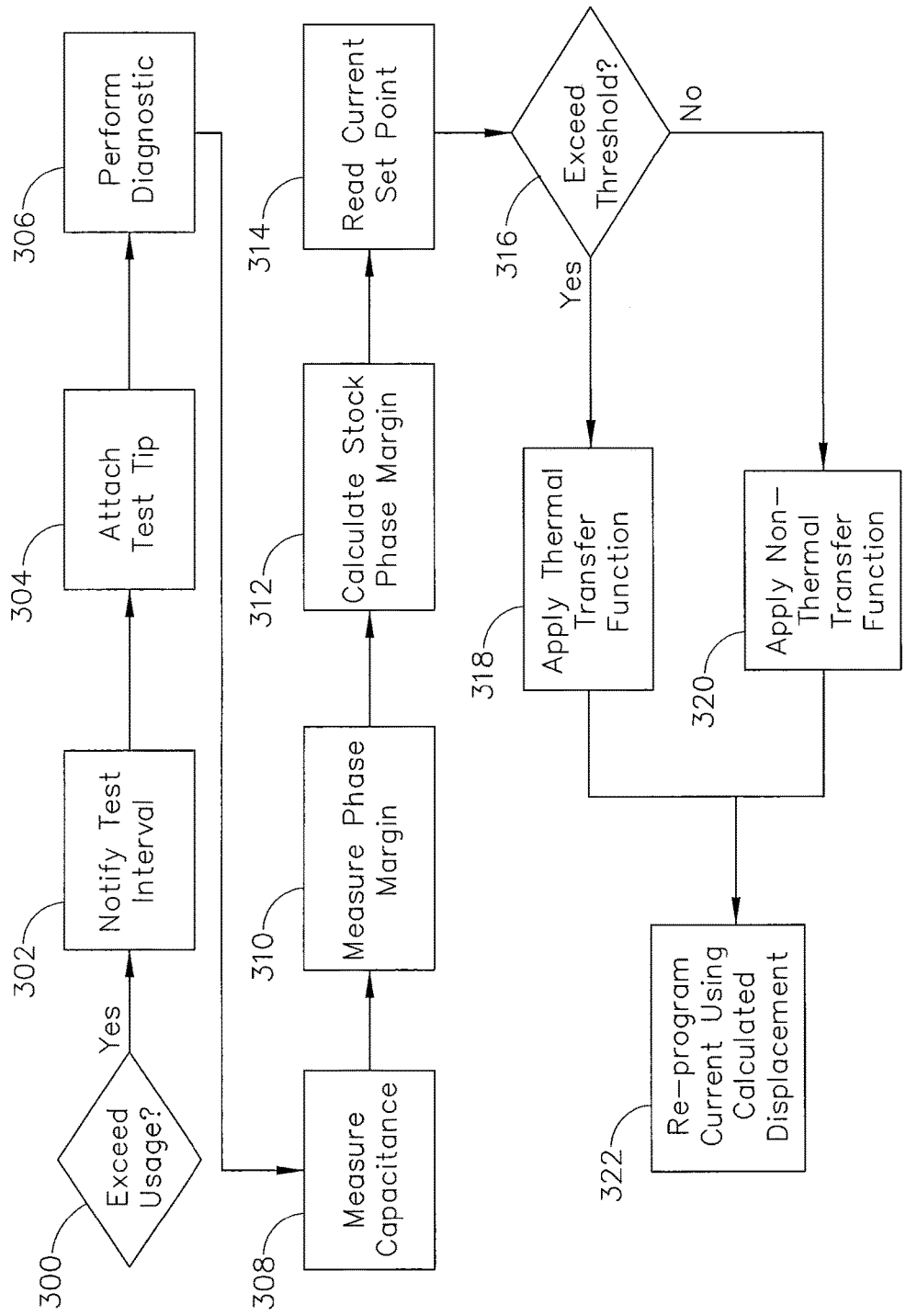
FIG. 3 depicts a flowchart of an exemplary set of steps that a system could perform to reprogram a surgical instrument based upon diagnostic data.

FIG. 3 shows a flowchart of an exemplary set of steps that a system could perform to reprogram a surgical instrument (100, 200) based upon diagnostic data. A generator (112) and surgical instrument (100, 200) may be configured to, when a surgical instrument (100, 200) usage counter reaches (block 300) a configured limit, generate a notification via generator (112) display (118) that a usage based test interval has been reached (block 302). Display (118) may also display a notification that a test interval is nearing, or display a counter indicating the number of uses remaining until the next test interval. Test intervals may be defined by a manufacturer or user, and there may be one or more test intervals for each different type of surgical instrument (100, 200), model number, model year, or geographic region, or the like. A test tip (not pictured) will be provided that may be attached (block 304) to a surgical instrument end effector (108, 214) to simulate normal usage during a procedure, and generator (112) may be configured to perform a diagnostic test (block 306) of surgical instrument (100, 200) with the attached test tip. In some versions, the test tip may include additional sensors for sensing one or more parameters during a diagnostic test, and may also have the capability to receive, process, and store data generated during a diagnostic test.

Figure 4:
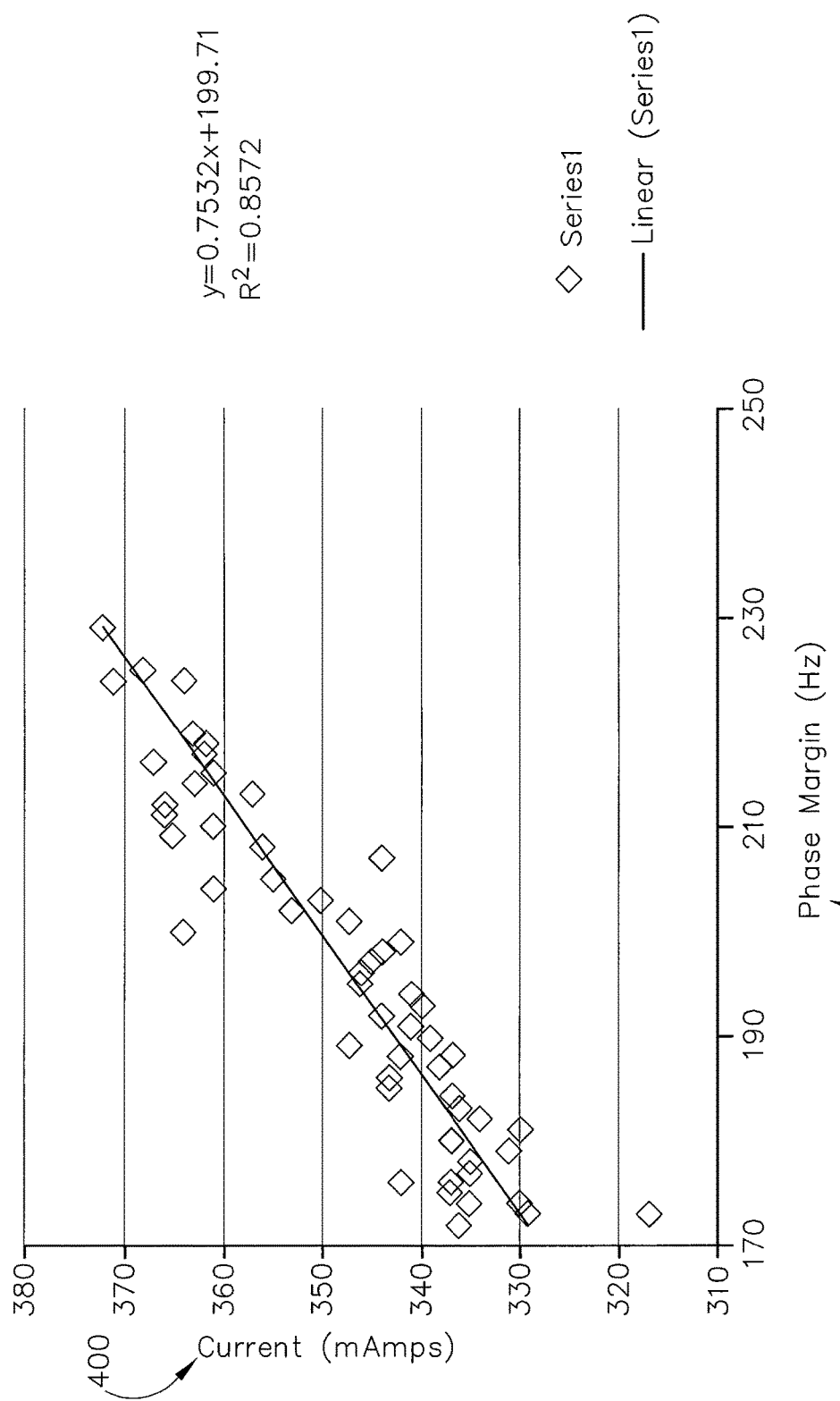
FIG. 4 depicts an exemplary graph plotting phase margin and current.

During the performance of the diagnostic test, generator (112), the test tip, or both will measure capacitance (block 308) and phase margin (block 310). By way of example only, current supplied during the test may be determined using the equation y=0.7532x+199.71, where x is measured phase margin in hertz and y is current in milliamps. FIG. 4 shows an exemplary visualization of this equation on a graph showing the relationship between phase margin (402) and current (400). As a surgical instrument (100, 200) is operated, displacement of the ultrasonic components increases and phase margin decreases. The difference between phase margin at the time of manufacture, or the stock phase margin, and the currently measured phase margin can be used to predict displacement of the ultrasonic components, while the manufactured phase margin can be determined using the equation Manufactured Phase Margin= (Current−199.7)/0.752. Displacement between current phase margin and manufactured phase margin can also be determined using the equation Disp.=(−0.0002*(Current Phase Margin)+0.103)*(0.7532*Manufactured Phase Margin)+198.7).

Figure 5:
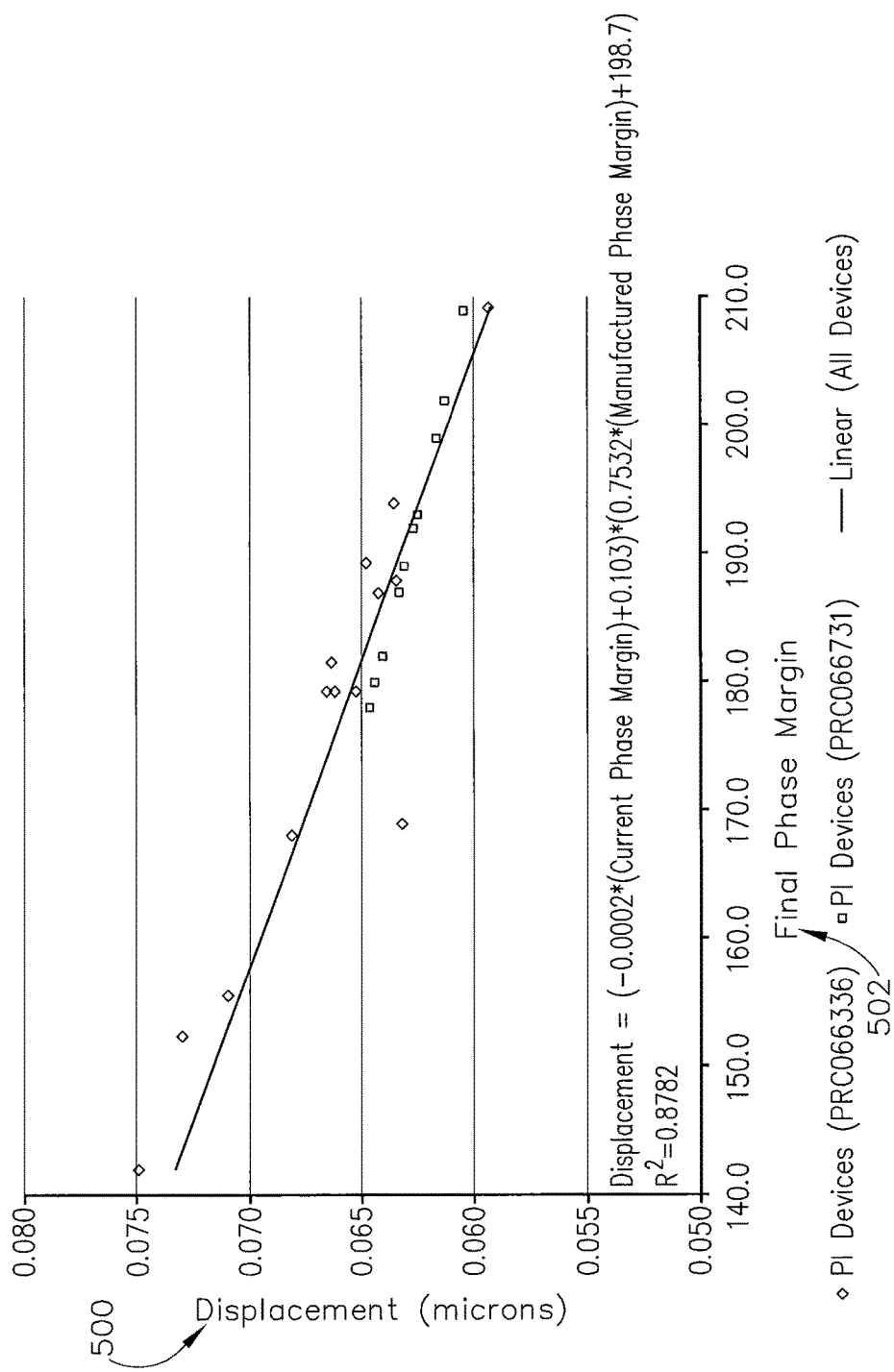
FIG. 5 depicts an exemplary graph plotting displacement and final phase margin.
Figure 6:
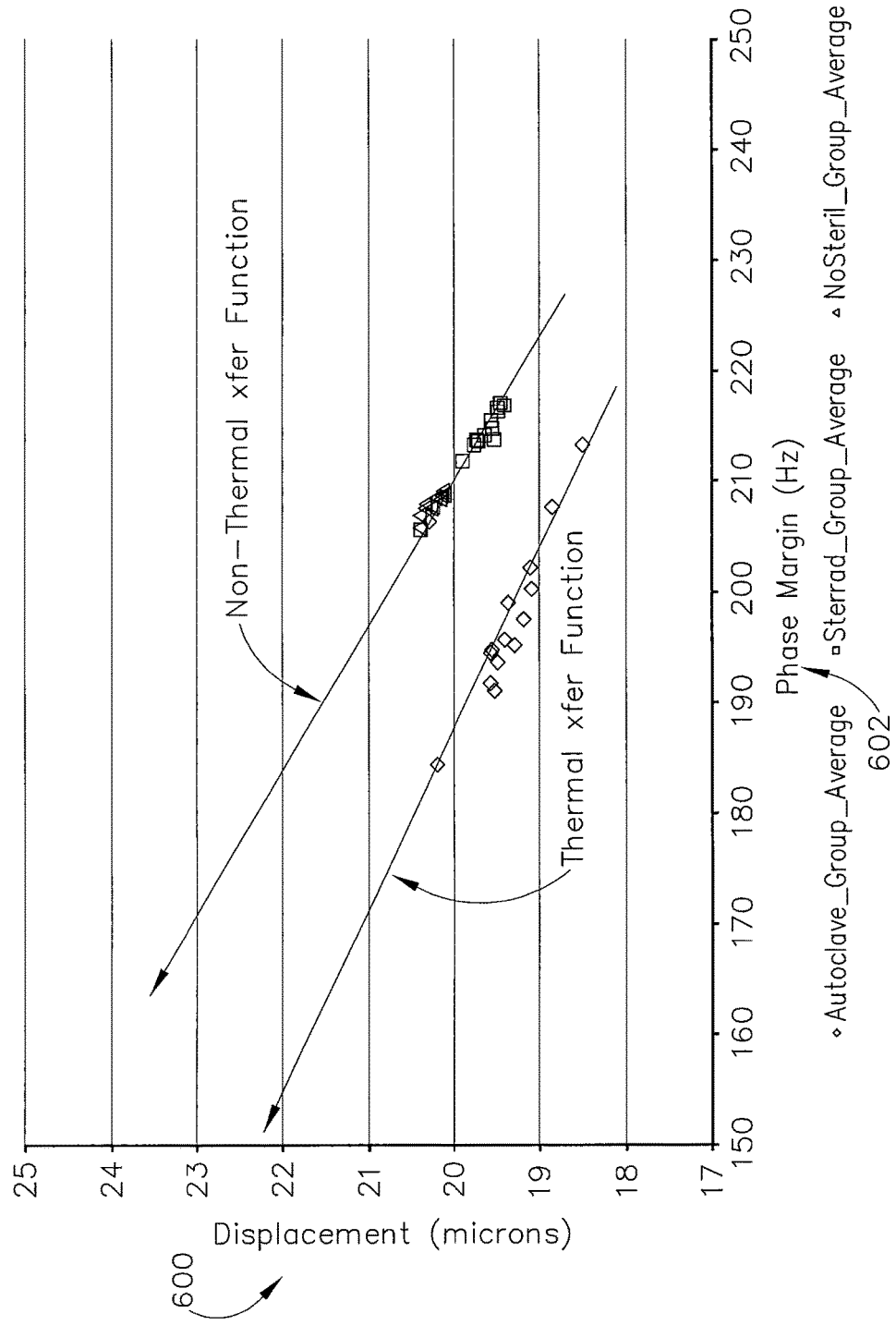
FIG. 6 depicts an exemplary graph plotting displacement and phase margin.

FIG. 5 shows an exemplary visualization of this equation on a graph showing the relationship between displacement (500) and final phase margin (502). Using the predicted displacements, a thermal transfer function can be used to determine optimal operational configuration for further uses. The accuracy of this determination can be greatly influenced by thermal exposure of surgical instrument (100, 200), either due to normal usage or due to autoclave sterilization procedures. As a result, using two different equations for determining phase margin versus displacement can improve accuracy, one for surgical instruments (100, 200) that have undergone thermal exposure and one for surgical instruments (100, 200) that have not exceeded a thermal exposure level. FIG. 6 shows an exemplary visualization of this concept on a graph showing the relationship between displacement (600) and phase margin (602) for each transfer function. Since the non-thermal transfer function results in a higher displacement for the same phase margin relative to the thermal transfer function by about 1.2 microns, it may account for the error in predicting displacement associated with phase margin shift. Therefore, it is helpful to identify when a transducer assembly (102, 210) has been exposed to an abusive thermal condition. This can be accomplished by identifying a change in capacitance of the transducer assembly (102, 210), as illustrated in FIG. 7, which shows the relationship between capacitance (700) and number of use cycles (702). FIG. 7 shows that a group of thermally exposed devices demonstrate a 0.5 nF jump in capacitance, while non-thermally exposed devices show a 0.2 nF jump in capacitance. Capacitance is measured at the time of production for each individual surgical instrument (100, 200) and may be stored in the EEPROM so that it can be used by generator (112) or other device during a lifecycle of surgical instrument (100, 200).

Continuing in light of the discussion above, once capacitance (block 308) and phase margin (block 310) are measured with the test tip, a phase margin at time of manufacture may be calculated using the equation Phase Margin=(current−199.7)/0.752 (block 312). Generator (112) will also read (block 314) a current set point from the EEPROM of surgical instrument (1014), and then reprogram the current based on a transfer function. A thermal transfer function (see Table 1 below) may be used (block 318) to determine the new optimal current if the measured capacitance exceeds (block 316) the original capacitance by about 0.5 nF. If the measured capacitance does not exceed (block 316) the original capacitance by about 0.5 nF, the non thermal transfer function (see Table 2 below) may be used (block 320) to determine the new optimal current.

TABLE 1

Exemplary Thermal Transfer Function $Displacement_{current} = (-0.00015) * (Phase\ Margin_{original}) * (Phase\ Margin_{current}) + (-0.03974) * (Phase\ Margin_{current}) + 0.080442 * (Phase\ Margin_{original}) + 20.22$ $$Current_{new} = \frac{(21.5 * Current_{original})}{Displacement_{current}}$$

TABLE 2

Exemplary Non-Thermal Transfer Function $Displacement_{current} = (-0.00015) * (Phase\ Margin_{original}) * (Phase\ Margin_{current}) + (-0.03974) * (Phase\ Margin_{current}) + 0.080442 * (Phase\ Margin_{original}) + 20.22 + 1.2$ $$Current_{new} = \frac{(21.5 * Current_{original})}{Displacement_{current}}$$

Once a new optimal current is determined using one of the transfer functions (block 318, block 320), surgical instrument (100, 200) may be reprogrammed using the optimal new current (block 322). Reprogramming may be accomplished by one or more of generator (112) or adaptor assembly (114, 504) and may be accomplished by rewriting the EEPROM of surgical instrument (100, 200). In effect, rewriting the EEPROM with a newly calculated optimal current to account for changes in displacement and phase margin as a result of normal use and thermal events may allow a surgical instrument (100, 200) to be returned to a condition and specification similar to that which it was manufactured to.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a reprogramming device comprising an instrument receptacle; (b) a surgical instrument comprising a generator connection and a memory, wherein the generator connection is configured to be connected to the instrument receptacle, wherein the memory is configured to store an original current value and an original phase margin value; and (c) a test tip configured to be connected to the surgical instrument, the test tip comprising a phase margin sensor; wherein the reprogramming device is configured to: (i) receive a set of phase margin data from the test tip, (ii) receive the original current value and the original phase margin value, (iii) determine a new current value based upon the set of phase margin data, the original current value, and the original phase margin value by using a transfer function, and (iv) write the new current value to the memory of the surgical instrument.

EXAMPLE 2

The apparatus of Example 1, wherein the reprogramming device is selected from the group consisting of: a surgical generator, a computer, a mobile computing device, and a removable power supply.

EXAMPLE 3

The apparatus of any of any one or more of Examples 1 through 2, wherein the surgical instrument comprises an ultrasonic surgical instrument.

EXAMPLE 4

The apparatus of any one or more of Examples 1 through 3, wherein the memory is configured to store an original capacitance value, wherein the test tip further comprises a capacitance sensor, wherein the reprogramming device is further configured to receive a set of capacitance data from the test tip, wherein the generator is further configured to: (i) determine a capacitance difference between the original capacitance value and the set of capacitance data, (ii) where the capacitance difference exceeds a thermal threshold, select a thermal transfer function as the transfer function, (iii) where the capacitance difference does not exceed a thermal threshold, select a non-thermal transfer function as the transfer function, and (iv) determine a displacement value based upon the original phase margin, the set of phase margin data, and the transfer function.

EXAMPLE 5

The apparatus of Example 4, wherein the thermal threshold is about 0.5 nF.

EXAMPLE 6

The apparatus of any one or more of Examples 4 through 5, wherein the displacement value is determined using the equation:

Displacement$_{current}$=(−0.00015)*(Phase Margin$_{original}$)*(Phase Margin$_{current}$)+(−0.03974)* (Phase Margin$_{current}$)+0.080442* (Phase Margin$_{original}$)+20.22, when the transfer function is a thermal transfer function.

EXAMPLE 7

The apparatus of any of any one or more of Examples 4 through 6, wherein the displacement value is determined using the equation:

Displacement$_{current}$=(−0.00015)*(Phase Margin$_{original}$)*(Phase Margin$_{current}$)+ (−0.03974)*(Phase Margin$_{current}$)+0.080442* (Phase Margin$_{original}$)+20.22+1.2, when the transfer function is a non-thermal transfer function.

EXAMPLE 8

The apparatus of any of any one or more of Examples 4 through 7, wherein the new current value is determined using the equation:

$$\text{Current}_{new} = \frac{(21.5 * \text{Current}_{original})}{\text{Displacement}_{current}}.$$

EXAMPLE 9

The apparatus of any of any one or more of Examples 1 through 8, wherein one or more of the surgical instrument or the reprogramming device are configured to: (i) prevent normal operation of the surgical instrument based upon the occurrence of a surgical instrument test interval, (ii) display a notification via a display, the notification indicating that the test tip should be attached to the surgical instrument, and (iii) resume normal operation of the surgical instrument after the reprogramming device writes the new current value to the memory of the surgical instrument.

EXAMPLE 10

The apparatus of Example 9, wherein the surgical instrument test interval is configured to occur based on a variable time interval stored on the memory of the surgical instrument.

EXAMPLE 11

A method comprising the steps: (a) measuring a phase margin of a surgical instrument with a test tip, wherein the test tip is configured to attach to the surgical instrument; (b) determining a displacement of the surgical instrument based upon the phase margin; (c) determining an optimized current using the displacement and a transfer function; and (d) configuring the surgical instrument to operate at the optimized current.

EXAMPLE 12

The method of Example 11, further comprising the steps: (a) storing an original capacitance in a memory of the surgical instrument; (b) measuring a current capacitance of the surgical instrument with the test tip; (c) determining a change in capacitance between the original capacitance and the current capacitance; and (d) selecting, as the transfer function, either a thermal transfer function or a non-thermal transfer function based upon the change in capacitance.

EXAMPLE 13

The method of Example 12, wherein the thermal transfer function is selected when change in capacitance exceeds 0.5 nF; and wherein the non-thermal transfer function is selected when the change in capacitance does not exceed 0.5 nF.

EXAMPLE 14

The method of any one or more of Examples 11 through 13, wherein determining a displacement of the surgical instrument based upon the phase margin comprises the steps: (i) calculating a stock phase margin of the surgical instrument based upon the phase margin, and (ii) calculating a displacement of the surgical instrument based upon the stock phase margin and the phase margin.

EXAMPLE 15

The method of any of any one or more of Examples 12 through 13, wherein the thermal transfer function is:

Displacement$_{current}$=(−0.00015)*(Phase Margin$_{original}$)*(Phase Margin$_{current}$)+ (−0.03974)*(Phase Margin$_{current}$)+0.080442* (Phase Margin$_{original}$)+20.22.

EXAMPLE 16

The method of any of any one or more of Examples 12 through 13 or 15, wherein the non-thermal transfer function is:

Displacement$_{current}$=(−0.00015)*(Phase Margin$_{original}$)*(Phase Margin$_{current}$)+ (−0.03974)*(Phase Margin$_{current}$)+0.080442* (Phase Margin$_{original}$)+20.22+1.2.

EXAMPLE 17

The method of any of any one or more of Examples 12 through 13 or 15 through 16 wherein the optimized current is determined using the equation:

$$\text{Current}_{new} = \frac{(21.5 * \text{Current}_{original})}{\text{Displacement}_{current}}.$$

EXAMPLE 18

The method of any one or more of Examples 11 through 17, further comprising the steps: (a) preventing normal operation of the surgical instrument based upon the occurrence of a surgical instrument test interval; (b) displaying a notification via a display, the notification indicating that the test tip should be attached to the surgical instrument; and (c) resuming normal operation of the surgical instrument after configuring the surgical instrument to operate at the optimal current.

EXAMPLE 19

The method of Example 18, wherein the surgical instrument test interval occurs about every 50 uses of the surgical instrument.

EXAMPLE 20

An apparatus comprising: (a) a reprogramming device comprising an instrument receptacle; (b) a surgical instrument comprising a generator connection and a memory, wherein the generator connection is configured to be connected to the instrument receptacle, wherein the memory is configured to store an original current value and an original phase margin value; and (c) a test tip configured to be connected to the surgical instrument, the test tip comprising a phase margin sensor; wherein the reprogramming device further comprises a means for configuring the surgical instrument with a new operating current based on diagnostic data.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

When used in the claims, a "means for configuring the surgical instrument with a new operating current based on diagnostic data" should be understood as a limitation set forth in the form of a means for performing a specified function as provided for in the sixth paragraph of 35 U.S.C. § 112 in which the specified function is "means for configuring the surgical instrument with a new operating current based on diagnostic data" and the corresponding structure is a processor and memory, where the processor and memory are programmed to read diagnostic data from one or more of the surgical instrument, surgical generator, or test tip, calculate a new operating current for the surgical instrument based upon a change in displacement of the surgical device from its original operating specification to its current operating specification, and configure the surgical instrument with the new operating current (examples provided in FIGS. 3-7 and paragraphs [0030]-[0034]).

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a reprogramming device comprising an instrument receptacle;
   (b) a surgical instrument comprising an end effector, a generator connection and a memory, wherein the generator connection is configured to be connected to the instrument receptacle, wherein the memory is configured to store an original current value; and
   (c) a test tip configured to be connected to the end effector;
   wherein the reprogramming device is configured to:
      (i) receive a set of phase margin data during a diagnostic operation of the surgical instrument with the test tip,
      (ii) determine an original phase margin value based on the original current value using a phase margin equation, and
      (iii) determine a displacement value based on the original phase margin value and a current phase margin value of the set of phase margin data using a transfer function,
      (iv) determine a new current value based upon the original current value and the displacement value, and
      (v) write the new current value to the memory of the surgical instrument, wherein the new current value is configured to be used by the surgical instrument to account for the displacement value during operation.

2. The apparatus of claim 1, wherein the reprogramming device is selected from the group consisting of: a surgical generator, a computer, a mobile computing device, and a removable power supply.

3. The apparatus of claim 1, wherein the surgical instrument comprises an ultrasonic surgical instrument.

4. The apparatus of claim 1, wherein the new current value is determined using the equation:

$$\text{Current}_{new} = \frac{(21.5 * \text{Current}_{original})}{\text{Displacement}_{current}}.$$

5. The apparatus of claim 1, wherein one or more of the surgical instrument or the reprogramming device are configured to:
   (i) prevent normal operation of the surgical instrument based upon the occurrence of a surgical instrument test interval,
   (ii) display a notification via a display, the notification indicating that the test tip should be attached to the surgical instrument, and
   (iii) resume normal operation of the surgical instrument after the reprogramming device writes the new current value to the memory of the surgical instrument.

6. The apparatus of claim 5, wherein the surgical instrument test interval is configured to occur based on a variable time interval stored on the memory of the surgical instrument.

7. The apparatus of claim 1, wherein the reprogramming device is configured to use the equation:

$$\text{Phase Margin}_{current} = (\text{Current}_{original} - 199.7)/0.752,$$

as the phase margin equation.

8. The apparatus of claim 1, wherein the reprogramming device is configured to provide an indication to a user that the new current value must be redetermined after about 50 uses of the surgical instrument.

9. The apparatus of claim 1, wherein the new current value is configured to cause the surgical instrument to operate with a reduced likelihood of mechanical failure as compared to the original current value.

10. The apparatus of claim 1, wherein the memory is further configured to store an original capacitance value, and the reprogramming device is further configured to:
    (a) receive a set of capacitance data during the diagnostic operation of the surgical instrument,
    (b) determine a capacitance difference between the original capacitance value and a current capacitance value of the set of capacitance data, and
    (c) select, as the transfer function, either a thermal transfer function or a non-thermal transfer function, based upon the capacitance difference.

11. The apparatus of claim 10, wherein, when the capacitance difference is greater than or equal to about 0.5 nF, the reprogramming device is configured to determine that the surgical instrument has been previously exposed to higher than typical heat levels.

12. The apparatus of claim 10, wherein the reprogramming device is configured to select the thermal transfer function as the transfer function when the capacitance difference is greater than or equal to about 0.5 nF.

13. The apparatus of claim 10, wherein the displacement value is determined using, as the transfer function, the equation:

$$\text{Displacement}_{current} = (-0.00015)*(\text{Phase Margin}_{original})*(\text{Phase Margin}_{current}) + (-0.03974)*(\text{Phase Margin}_{current}) + 0.080442*(\text{Phase Margin}_{original}) + 20.22,$$

when the transfer function is a thermal transfer function.

14. The apparatus of claim 10, wherein the displacement value is determined using, as the transfer function, the equation:

$$\text{Displacement}_{current} = (-0.00015)*(\text{Phase Margin}_{original})*(\text{Phase Margin}_{current}) + (-0.03974)*(\text{Phase Margin}_{current}) + 0.080442*(\text{Phase Margin}_{original}) + 20.22 + 1.2,$$

when the transfer function is a non-thermal transfer function.

15. A surgical instrument reprogramming device comprising:
    (a) an instrument receptacle; and
    (b) a processor configured to operate and communicate with a surgical instrument when the surgical instrument is attached to the instrument receptacle;
    wherein the processor is configured to:
    (i) cause the surgical instrument to perform a diagnostic operation of an end effector of the surgical instrument and generate a set of phase margin data and a set of capacitance data during the diagnostic operation,
    (ii) receive an original current value and an original capacitance value from a memory of the surgical instrument,
    (iii) determine:
       (A) an original phase margin value based on the original current value using a phase margin equation, and
       (B) a capacitance difference between the original capacitance value and a current capacitance value of the set of capacitance data,
    (iv) select, as a transfer function, either a thermal transfer function or a nonthermal transfer function, based upon the capacitance difference, (v) determine a displacement value based on the original phase margin value and a current phase margin value of the set of phase margin data using the transfer function,
(vi) determine a new current value based upon the original current value and the displacement value, and
(vii) write the new current value to the memory of the surgical instrument, wherein the new current value is configured to be used by the surgical instrument to account for the displacement value during operation.

\* \* \* \* \*